(12) United States Patent
Altay et al.

(10) Patent No.: US 11,655,408 B2
(45) Date of Patent: May 23, 2023

(54) GEL COMPOSITION COMPRISING A PHASE CHANGE MATERIAL

(71) Applicant: Croda International PLC, East Yorkshire (GB)

(72) Inventors: Altug Altay, East Yorkshire (GB); Marco Maria Auerbach, East Yorkshire (GB)

(73) Assignee: CRODA INTERNATIONAL PLC, Goole (GB)

( * ) Notice: Subject to any disclaimer, the term of this patent is extended or adjusted under 35 U.S.C. 154(b) by 495 days.

(21) Appl. No.: 16/652,806

(22) PCT Filed: Sep. 18, 2018

(86) PCT No.: PCT/EP2018/075237
§ 371 (c)(1),
(2) Date: Apr. 1, 2020

(87) PCT Pub. No.: WO2019/068458
PCT Pub. Date: Apr. 11, 2019

(65) Prior Publication Data
US 2020/0231857 A1    Jul. 23, 2020

(30) Foreign Application Priority Data
Oct. 2, 2017 (GB) .................................. 1715950

(51) Int. Cl.
| C09K 5/06 | (2006.01) |
| C08L 53/00 | (2006.01) |
| C08K 3/36 | (2006.01) |
| B01J 13/00 | (2006.01) |
| C08L 25/08 | (2006.01) |
| C08K 5/053 | (2006.01) |
| C08K 5/09 | (2006.01) |

(52) U.S. Cl.
CPC ............ *C09K 5/063* (2013.01); *B01J 13/0065* (2013.01); *C08K 3/36* (2013.01); *C08L 25/08* (2013.01); *C08L 53/00* (2013.01); *C08K 5/053* (2013.01); *C08K 5/09* (2013.01); *C08L 2205/24* (2013.01)

(58) Field of Classification Search
CPC ............ C08L 25/08; C08L 53/00; C09K 5/06
See application file for complete search history.

(56) References Cited

U.S. PATENT DOCUMENTS

| 4,825,939 A * | 5/1989 | Salyer ................... F28D 20/023 165/53 |
| 7,320,770 B2 * | 1/2008 | Chomard ................... C08J 3/09 264/262 |
| 7,468,411 B2 * | 12/2008 | Smith ................ C08G 18/3206 524/297 |
| 8,933,139 B1 * | 1/2015 | Peterson ............ C08G 18/7664 521/70 |
| 8,933,140 B2 * | 1/2015 | Peterson ................ C08J 9/0014 521/70 |
| 9,080,051 B2 * | 7/2015 | Peterson ................ C08J 9/0014 |
| 9,260,645 B2 * | 2/2016 | Bruzda ................... H01L 23/42 |
| 9,315,648 B2 * | 4/2016 | Nilson ...................... C08K 5/01 |
| 9,556,373 B2 * | 1/2017 | Formato .................. C09K 5/06 |
| 9,596,822 B2 * | 3/2017 | Lewis ..................... A24B 13/02 |
| 9,771,508 B2 * | 9/2017 | Bruzda ................... H01L 23/42 |
| 9,914,865 B2 * | 3/2018 | Sawafta ................. C09K 5/063 |
| 2006/0124892 A1 * | 6/2006 | Rolland ................ B32B 15/085 252/70 |
| 2013/0298991 A1 * | 11/2013 | Parker ..................... C09K 5/02 136/259 |
| 2014/0290285 A1 | 10/2014 | Formato et al. |

FOREIGN PATENT DOCUMENTS

| CN | 1491270 A | 4/2004 | |
| DE | 10 2016 013 415 A1 * | 5/2018 | ............... C09K 5/06 |
| JP | 2004-079641 A | 3/2004 | |
| JP | 2014-122320 A | 7/2014 | |
| JP | 2018-515520 A | 6/2018 | |
| WO | 0026285 A1 | 5/2000 | |
| WO | WO 2002/062918 A1 | 8/2002 | |
| WO | WO 2016/180870 A1 | 11/2016 | |

OTHER PUBLICATIONS

Zhao Lin et al: Rheological properties search of SiO2/PEG dispersion system, "Guangzhou Chemical", vol. 39 part 1, 2011, pp. 76-78.

International Application No. PCT/EP2018/075237, International Search Report and Written Opinion dated Dec. 19, 2018, 9 pages.

* cited by examiner

*Primary Examiner* — Rip A Lee

(74) *Attorney, Agent, or Firm* — BakerHostetler

(57) ABSTRACT

The present invention provides a composition comprising a) a phase change material; b) 1 to 10 wt % of a silica gelling additive; and c) a styrene co-polymer gelling additive; wherein the composition is in the form of a gel and wherein the weight ratio of b) silica gelling additive to c) styrene co-polymer gelling additive in the composition is in the range from 0.6 to 5:1. The invention also provides a method of making the composition and an article and a product comprising the composition. Finally, the invention provides the use of a combination of a silica gelling additive and a styrene co-polymer gelling additive to make a gel composition comprising a phase change material with one or more improved properties.

14 Claims, No Drawings

GEL COMPOSITION COMPRISING A PHASE CHANGE MATERIAL

CROSS-REFERENCE TO RELATED APPLICATIONS

This application is the National Stage of International Patent Application No. PCT/EP2018/075237 filed Sep. 18, 2018, which claims priority from Great Britain Patent Application No. 1715950.0, filed Oct. 2, 2017, the disclosures of each of which are incorporated herein by reference in their entireties for any and all purposes.

FIELD OF THE INVENTION

The present invention relates to a composition comprising a phase change material (PCM) which is in the form of a gel, a method of making the gel composition, an article or product comprising the composition and the use of a combination of a silica gelling additive and a styrene co-polymer gelling additive to make a gel composition.

BACKGROUND

Phase change materials (PCMs) are a class of material which may be used as latent heat storage media, heat transfer media and/or temperature regulating media. PCMs find many applications; for example, as heat storage media in insulating materials or building materials or as heat transfer media in heating and cooling systems (e.g. in air-conditioning, refrigeration or automotive applications), or as temperature regulating media (e.g. in temperature sensitive applications such as packaging, clothing and bedding/mattresses). The way in which PCMs operate is based on the enthalpy of transformation accompanying the transition of the PCM from the solid to the liquid phase or vice versa, which results in energy being absorbed from or released to its surroundings. In this way, PCMs can be used for maintaining a constant temperature within a defined range and/or for improving heat insulation.

One application of PCMs is in the building and construction industry, offering the possibility to reduce the use of heating and air conditioning, and to maintain a comfortable temperature in light-weight buildings with low thermal mass. Other applications include the capture and use of low-grade heat from industrial processes or machinery such as engines, storage of solar energy, and temperature regulation of temperature sensitive material including food, living organisms such as people and animals, pharmaceutical and biological material, transplant organs and delicate electronics.

Since one phase of a PCM is a liquid phase and another phase is solid, PCMs require careful storage and containment during their use to avoid leakage. A need remains to improve one or more properties of a composition comprising a phase change material to improve its performance or ease of containment.

SUMMARY OF THE INVENTION

The present invention is based in part on the recognition by the applicant that an advantageous combination of gelling agents can be used to gel a composition comprising a phase change material. Without being bound by theory, the combination of a silica gelling additive and a styrene co-polymer gelling additive provides advantages to the composition due to the different mechanisms by which these additives provide a gelling effect.

Thus viewed from a first aspect the present invention provides a composition comprising:
  a) a phase change material;
  b) 1 to 10 wt % of a silica gelling additive; and
  c) a styrene co-polymer gelling additive;
wherein the composition is in the form of a gel and wherein the weight ratio of b) silica gelling additive to c) styrene co-polymer gelling additive in the composition is in the range from 0.6 to 5:1.

Viewed from a second aspect the present invention provides an article comprising a sealed container and a composition according to the first aspect contained within the container.

Viewed from a third aspect the present invention provides a method of making a composition according to the first aspect comprising the steps of:
  i) mixing the components of the composition at a sufficient temperature and for a sufficient time to allow the styrene co-polymer gelling additive to completely dissolve in the composition; and
  ii) stopping mixing to allow the composition to rest and to form a gel.

Viewed from a fourth aspect the present invention provides the use of a combination of a silica gelling additive and a styrene co-polymer gelling additive to make a gel composition comprising a phase change material wherein the flow at rest (FAR) period at 25° C., as measured herein, of the gel composition is at least 2 times longer than that of a comparative gel composition wherein the comparative gel composition comprises a comparative gelling additive consisting solely of the styrene co-polymer, wherein the total wt % of gelling additives in the gel composition and in the comparative gel composition is equivalent.

Viewed from a fifth aspect the present invention provides the use of a combination of a silica gelling additive and a styrene co-polymer gelling additive to make a gel composition comprising a phase change material wherein the shear thinning value (STV) at 25° C., as measured herein, of the gel composition is at least 2 times greater than that of a comparative gel composition wherein the comparative gel composition comprises a comparative gelling additive consisting solely of the styrene co-polymer, wherein the total wt % of gelling additives in the gel composition and in the comparative gel composition is equivalent.

Any aspect of the invention may include any of the features described herein with regard to that aspect of the invention or any other aspects of the invention.

DETAILED DESCRIPTION OF THE INVENTION

It will be understood that any upper or lower quantity or range limit used herein may be independently combined.

When used herein, it will be understood that the term "wt %" refers to the percentage by weight of the specified component on the basis of the total weight of the specified entity which the component is part of.

It will be understood that, when describing the number of carbon atoms in a substituent group (e.g. 'C1 to C6'), the number refers to the total number of carbon atoms present in the substituent group, including any present in any branched groups. Additionally, when describing the total number of carbon atoms in, for example fatty acids, this refers to the total number of carbon atoms including the one at the carboxylic acid, and any present in any branch groups.

Many of the chemicals which may be used to produce the present invention are obtained from natural sources. Such chemicals typically include a mixture of chemical species due to their natural origin. Due to the presence of such mixtures, various parameters defined herein can be an average value and may be non-integral.

Component a) Phase Change Material (PCM)

The PCM may be organic. The PCM may be polymeric or non-polymeric. Preferably the PCM is organic and non-polymeric. The PCM may not comprise a hydrocarbon. The PCM may not comprise an alkane. The PCM may not comprise tetradecane, hexadecane or octadecane.

Preferably the phase change material is selected from the group consisting of fatty acids, fatty alcohols, fatty amines, fatty acid esters, fatty alcohol esters, fatty acid amides and mixtures thereof.

The PCM may comprise an ester, preferably consists of an ester. The PCM may comprise a mixture of a first ester and a second ester. The PCM ester may comprise a linear alcohol reactant. The PCM ester may comprise a linear carboxylic acid reactant. Preferably the PCM ester comprises a linear alcohol reactant and a linear carboxylic acid reactant. The PCM ester may comprise a mono-alcohol reactant. The PCM ester may comprise a mono-carboxylic acid reactant. Preferably the PCM ester comprises a mono-alcohol reactant and a mono-carboxylic acid reactant. Preferably the PCM comprises a fatty acid ester or a fatty alcohol ester, more preferably a fatty acid ester. The PCM may comprise, preferably consists of, a fatty acid ester or a mixture of fatty acid esters.

The PCM may be selected from the group consisting of methyl octanoate, methyl decanoate, methyl undecanoate, methyl laurate, methyl myristate, methyl palmitate, methyl stearate, methyl arachidate, methyl behenate, ethyl octanoate, ethyl decanoate, ethyl undecanoate, ethyl laurate, ethyl myristate, ethyl palmitate, ethyl stearate, ethyl arachidate, ethyl behenate and mixtures thereof.

The PCM may be selected from the group consisting of propyl octanoate, propyl decanoate, propyl undecanoate, propyl laurate, propyl myristate, propyl palmitate, propyl stearate, propyl arachidate, propyl behenate, butyl octanoate, butyl decanoate, butyl undecanoate, butyl laurate, butyl myristate, butyl palmitate, butyl stearate, butyl arachidate, butyl behenate and mixtures thereof.

The PCM may be selected from the group consisting of pentyl octanoate, pentyl decanoate, pentyl undecanoate, pentyl laurate, pentyl myristate, pentyl palmitate, pentyl stearate, pentyl arachidate, pentyl behenate, hexyl octanoate, hexyl decanoate, hexyl undecanoate, hexyl laurate, hexyl myristate, hexyl palmitate, hexyl stearate, hexyl arachidate, hexyl behenate and mixtures thereof.

The PCM may be selected from the group consisting of heptyl octanoate, heptyl pelargonate, heptyl decanoate, heptyl undecanoate, heptyl laurate, heptyl myristate, heptyl palmitate, heptyl stearate, heptyl arachidate, heptyl behenate, octyl heptanoate, octyl octanoate, octyl pelargonate, octyl decanoate, octyl undecanoate, octyl laurate, octyl myristate, octyl palmitate, octyl stearate, octyl arachidate, octyl behenate and mixtures thereof.

The PCM may be selected from the group consisting of nonyl propionate, nonyl butanoate, nonyl pentanoate, nonyl hexanoate, nonyl heptanoate, nonyl octanoate, nonyl pelargonate, nonyl decanoate, nonyl undecanoate, nonyl laurate, nonyl myristate, nonyl palmitate, nonyl stearate, nonyl arachidate, nonyl behenate, decyl acetate, decyl propionate, decyl butanoate, decyl pentanoate, decyl hexanoate, decyl heptanoate, decyl octanoate, decyl pelargonate, decyl decanoate, decyl undecanoate, decyl laurate, decyl myristate, decyl palmitate, decyl stearate, decyl arachidate, decyl behenate and mixtures thereof.

The PCM may be selected from the group consisting of lauryl formate, lauryl acetate, lauryl propionate, lauryl butanoate, lauryl pentanoate, lauryl hexanoate, lauryl heptanoate, lauryl octanoate, lauryl pelargonate, lauryl decanoate, lauryl undecanoate, lauryl laurate, lauryl myristate, lauryl palmitate, lauryl stearate, lauryl arachidate, lauryl behenate and mixtures thereof.

The PCM may be selected from the group consisting of myristyl formate, myristyl acetate, myristyl propionate, myristyl butanoate, myristyl pentanoate, myristyl hexanoate, myristyl heptanoate, myristyl octanoate, myristyl pelargonate, myristyl decanoate, myristyl undecanoate, myristyl laurate, myristyl myristate, myristyl palmitate, myristyl stearate, myristyl arachidate, myristyl behenate and mixtures thereof.

The PCM may be selected from the group consisting of cetyl formate, cetyl acetate, cetyl propionate, cetyl butanoate, cetyl pentanoate, cetyl hexanoate, cetyl heptanoate, cetyl octanoate, cetyl pelargonate, cetyl decanoate, cetyl undecanoate, cetyl laurate, cetyl myristate, cetyl palmitate, cetyl stearate, cetyl arachidate, cetyl behenate and mixtures thereof.

The PCM may be selected from the group consisting of stearyl formate, stearyl acetate, stearyl propionate, stearyl butanoate, stearyl pentanoate, stearyl hexanoate, stearyl heptanoate, stearyl octanoate, stearyl pelargonate, stearyl decanoate, stearyl undecanoate, stearyl laurate, stearyl myristate, stearyl palmitate, stearyl stearate, stearyl arachidate, stearyl behenate and mixtures thereof.

The PCM may be selected from the group consisting of butyl decanoate, methyl laurate, octyl laurate, lauryl laurate, lauryl pelargonate, octyl myristate, myristyl pelargonate, nonyl laurate, methyl myristate, decyl laurate, octyl palmitate, lauryl caprate, cetyl octanoate, methyl palmitate, methyl stearate, lauryl laurate, octyl stearate, decyl palmitate, stearyl pelargonate, lauryl myristate, decyl stearate, stearyl caprate, cetyl palmitate, behenyl behenate and mixtures thereof.

Component b) Silica Gelling Additive

The silica gelling additive may comprise one or more types of silica. The silica gelling additive may comprise polymeric silica, fumed silica and/or precipitated silica. The silica gelling additive may comprise hydrophilic silica and/or hydrophobic silica.

Useful silicas in the present invention are polymeric silicas, precipitated silicas, fumed silicas, colloidal silicas and/or thermal silicas. These synthetic silicas may be amorphous. Preferred silicas comprise hydrophobic and hydrophilic fumed silicas, and mixtures thereof. Preferably the silica gelling additive is a fumed silica.

Examples of commercially available fumed silicas include the Aerosil® series (Evonik Corporation, Parsippany, N.J.), Cab-O-Sil® series (Cabot Corporation, Billerica, Mass.), and HDK® series (Wacker Chemical Corporation, Adrian, Mich.) product lines.

The particle size of the silicas referenced herein indicates the median particle diameter (d50) as determined by laser diffraction. Although the fumed silica particles are generally smaller than precipitated silicas, this is not always the case as they can form agglomerates well in excess of 10 µm. Silicas with smaller particle size and having increased surface area generally have increased thickening ability. One of the main differences between fumed and precipitated silicas is the presence of a higher density of silanol groups on the surface of precipitated silicas.

Various particle sizes of the silica are useful in this invention. Useful silica particle sizes include from about 0.01 μm to about 200 μm, from about 0.01 μm to about 100 μm, from about 0.01 μm to about 60 μm, from about 0.1 μm to about 200 μm, from about 0.1 μm to about 100 μm, from about 0.1 μm to about 60 μm, from about 0.5 μm to about 200 μm, from about 0.5 μm to about 100 μm, from about 0.5 μm to about 60 μm, from about 1 μm to about 200 μm, from about 1 μm to about 100 μm, from about 1 μm to about 60 μm.

Component c) Styrene Co-Polymer Gelling Additive

The styrene co-polymer gelling additive may comprise at least one co-polymer of styrene (S) and polyolefin. The polyolefin may be ethylene-propylene (EP) or ethylene-butylene (EB). The styrene co-polymer may comprise a di-block and/or tri-block co-polymer. The tri-block co-polymers may have a (poly)styrene (S) block on both ends of the chain and a (poly)ethylene-propylene (EP) or (poly)ethylene-butylene (EB) block in the middle whereas the di-block structure has a styrene block on only one end of the chain. Styrene may also be incorporated into the polyolefin block.

The styrene co-polymer may comprise a SEP, SEB, SEPS or SEBS co-polymer or mixtures thereof, with or without styrene incorporated into the polyolefin block. Preferably the styrene co-polymer gelling additive is selected from styrene-(ethylene-propylene)-styrene (SEPS) tri-block co-polymers, styrene-(ethylene-butylene)-styrene (SEBS) tri-block co-polymers and mixtures thereof. Preferably the styrene co-polymer has styrene incorporated into the polyolefin block.

The styrene co-polymer may be available from Kraton Corporation under the tradenames Kraton G, Kraton D, Kraton A co-polymers which have a di-block, tri-block, star-shaped or arm structure. It is understood that Kraton G series do not have styrene incorporated into the polyolefin block, while Kraton A series do. The styrene co-polymer may be available from Kuraray America, Inc. under the tradename Septon.

The styrene co-polymer may comprise a mixture of the above mentioned polymers.

The styrene blocks of the co-polymer may form micro-phase separated domains in the PCM composition and serve as cross-linking points on the three dimensional structure. The polyolefin block may partially dissolve in the PCM and entrap the material. The styrene co-polymer preferably comprises a high molecular weight tri-block copolymer that forms denser cross-linking points. Among the said copolymer types, Kraton A polymers which contain styrene blocks integrated to the polyolefin block were found to be particularly advantageous in gelling.

Optional Component d) Diol

The composition may further comprise 0.05 to 10 wt % of a diol. The composition may comprise at least 0.1 wt % of the diol, preferably at least 0.15 wt %, more preferably at least 0.2 wt %, particularly at least 0.25 wt %. The composition may comprise at most 10 wt % of the diol, preferably at most 8 wt %, more preferably at most 6 wt %, particularly at most 4 wt %, desirably at most 2 wt %.

The diol may advantageously interact with the silica gelling additive and strengthen the silica internal network. The diol may increase the viscosity of the composition, especially at temperatures above 25° C., The diol may reduce or prevent a reduction in the viscosity of the composition in the temperature range from 25° C. to 80° C., preferably from 25° C. to 60° C., more preferably from 25° C. to 40° C.

Preferably the diol is selected from alkylene glycols, polyalkylene glycols, polyoxyalkylene co-polymers and mixtures thereof.

Preferably the diol is a polyethylene glycol, more preferably a polyethylene glycol with a molecular weight in the range from 200 to 1000 i.e. $PEG_{200}$ to $PEG_{1000}$ Other Optional Components A nucleating agent may be included in the composition to prevent sub-cooling of the PCM. The nucleating agent may have a higher melting point than the PCM. The nucleating agent may be organic or inorganic, preferably organic. The nucleating agent may be selected from fatty acids, fatty alcohols, fatty amines, fatty acid esters, mono-, di- and tri-glycerides, polyethers, and mixtures thereof, preferably selected from fatty acids, fatty alcohols, fatty amines, fatty acid esters and mixtures thereof. The nucleating agent may be a wax. The nucleating agent may be selected from behenyl behenate, lauric acid, myristic acid, palmitic acid, stearic acid, arachidic acid, behenic acid, stearyl alcohol, stearamide, squalane wax, beeswax, montane wax, petroleum wax, microcrystalline wax, polyethylene wax, diatomaceous earth, graphite, potassium dihydrogen phosphate, calcium sulfate and mixtures thereof. The nucleating agent may have a melting point at least 10° C. higher than that of the PCM, preferably at least 15° C. higher, particularly at least 20° C. higher, desirably at least 30° C. higher. The nucleating agent may have a melting point at most 100° C. higher than that of the PCM, preferably at most 50° C. higher.

A thermal stabilizer may be required to preventing or retard thermally induced decomposition or isomerization of the PCM composition. In particular, a thermal stabilizer may prevent or retard formation of lower molecular weight products or isomers resulting from thermally induced decomposition or isomerization of the ester. The thermal stabilizer may be selected from phosphites, phosphonites, phosphate esters and mixtures thereof.

An anti-oxidant may be required to prevent or retard oxidation of the PCM composition. In particular, an anti-oxidant may prevent or retard formation of products resulting from reaction of the ester with atmospheric oxygen or with oxygen free radicals, which products may include, for example, alcohols, aldehydes, acids, peroxides, or water. The anti-oxidant may be selected from phenolic antioxidants, sterically hindered phenolic antioxidants, thioether antioxidants, aminic antioxidants, and mixtures thereof.

A fire retardant may be required for fire safety purposes or to conform with fire safety regulations for some uses of the PCM composition. The fire retardant may be selected from a halogenated hydrocarbon, a phosphate ester and mixtures thereof. The fire retardant may be selected from chloroparaffin, bromooctadecane, bromopentadecane, bromononadecane, bromoeicosane, bromodocosane and mixtures thereof. Other possible flame retardants include bis(pentabromophenyl) oxide or bis(tetrabromophenyl) oxide.

A heat transfer enhancing agent may be included in the composition. The heat transfer enhancing agent may be selected from graphitic, metal and metal oxide particles and/or powders.

Amounts and Proportions of Components in Composition

The composition of the invention may comprise at least 50 wt % of PCM, preferably at least 60 wt %, more preferably at least 70 wt %, particularly at least 80 wt %, desirably at least 85 wt %, especially at least 90 wt %.

The composition comprises from 1 to 10 wt % of the silica gelling additive. The composition may comprise at least 1.5 wt % of the silica gelling additive, preferably at least 2 wt %, more preferably at least 3 wt %, particularly at least 4 wt %. The composition may comprise at most 9 wt % of the silica gelling additive, preferably at most 8 wt %, more preferably at most 7 wt %, particularly at most 6 wt %.

The weight ratio of b) silica gelling additive to c) styrene co-polymer gelling additive in the composition is in the range from 0.6 to 5:1. This weight ratio range may provide an advantageous combination of the presence of a silica internal network provided by the silica gelling additive and a styrene co-polymer internal network provided by the styrene co-polymer gelling additive. The combination of the different properties of these internal networks within this weight ratio range may provide beneficial properties to the composition. Without being bound by theory, a lower weight ratio than 0.6:1 may result in the higher concentration of styrene co-polymer reducing the effect of the silica internal network while a higher weight ratio than 5:1 may result in the higher concentration of silica reducing the effect of the styrene co-polymer internal network.

The weight ratio of b) silica gelling additive to c) styrene co-polymer gelling additive in the composition may be at least 0.8:1, preferably at least 1:1, more preferably at least 1.2:1, particularly at least 1.4:1, desirably at least 1.5:1. The weight ratio of b) silica gelling additive to c) styrene co-polymer gelling additive in the composition may be at most 4.5:1, preferably at most 4:1, more preferably at most 3.5:1, particularly at most 3:1, desirably at most 2.5:1.

The composition may comprise at least 0.2 wt % of the styrene co-polymer gelling additive, preferably at least 0.6 wt %, more preferably at least 1 wt %, particularly at least 2 wt %. The composition may comprise at most 16 wt % of the styrene co-polymer gelling additive, preferably at most 12 wt %, more preferably at most 8 wt %, particularly at most 6 wt %, desirably at most 4 wt %.

The composition may comprise at least 0.1 wt % of nucleating agent, preferably at least 1 wt %, particularly at least 2 wt %. The composition may comprise at most 10 wt % of nucleating agent, preferably at most 8 wt %, particularly at most 6 wt %, desirably at most 4 wt %.

The composition may comprise at least 0.1 wt % of thermal stabilizer, preferably at least 1 wt %, particularly at least 2 wt %. The composition may comprise at most 10 wt % of thermal stabilizer, preferably at most 8 wt %, particularly at most 6 wt %, desirably at most 4 wt %.

The composition may comprise at least 0.1 wt % of anti-oxidant, preferably at least 1 wt %, particularly at least 2 wt %. The composition may comprise at most 10 wt % of anti-oxidant, preferably at most 8 wt %, particularly at most 6 wt %, desirably at most 4 wt %.

The composition may comprise at least 0.1 wt % of fire retardant, preferably at least 1 wt %, particularly at least 2 wt %. The composition may comprise at most 10 wt % of fire retardant, preferably at most 8 wt %, particularly at most 6 wt %, desirably at most 4 wt %.

The composition may comprise at least 0.1 wt % of heat transfer enhancing agent, preferably at least 1 wt %, particularly at least 2 wt %. The composition may comprise at most 10 wt % of heat transfer enhancing agent, preferably at most 8 wt %, particularly at most 6 wt %, desirably at most 4 wt %.

Composition Properties

The composition is in the form of a gel. The composition may be a gel, preferably a form-stable gel. The gel may comprise at least one internal network provided by the gelling additives. The internal network may structure the gel. The gel may comprise a silica internal network provided by the silica gelling additive and a styrene co-polymer internal network provided by the styrene co-polymer gelling additive. The composition may be a non-Newtonian fluid. The composition may be shear-thinning.

The composition may have a Shear Thinning Value (STV) at a reference temperature, which may be calculated as:

$$\text{STV} = \text{viscosity at } 0.2 \text{ s}^{-1} / \text{viscosity at } 59 \text{ s}^{-1}$$

the viscosity being measured at the reference temperature on a DHR-2 Rheometer from TA Instruments with a 40 mm stainless steel parallel plate geometry.

The composition may have a STV at 25° C. of at least 20, preferably at least 40, more preferably at least 60, particularly at least 80, desirably at least 100. The composition may have a STV at 25° C. of at most 500, preferably at most 400, more preferably at most 300.

The composition may have a STV at 40° C. of at least 20, preferably at least 40, more preferably at least 60, particularly at least 80, desirably at least 100. The composition may have a STV at 25° C. of at most 500, preferably at most 400.

The composition may have a Flow At Rest (FAR) at a reference temperature, which may be measured by placing an amount of the composition in a plastic conical funnel with a circular lower (outlet) aperture of 0.9 cm diameter, a circular upper (inlet) aperture of 6.8 cm diameter and a height of 5 cm. The FAR is the time elapsed for 85 wt % of the sample to flow through the outlet aperture.

The composition may have a FAR at 25° C. of at least 30 mins, preferably at least 60 mins, more preferably at least 2 hours, particularly at least 4 hours, desirably at least 12 hours, especially at least 20 hours.

The composition may have a FAR at 40° C. of at least 30 mins, preferably at least 60 mins, more preferably at least 2 hours, particularly at least 4 hours, desirably at least 12 hours, especially at least 20 hours.

The weight ratio of b) silica gelling additive to c) styrene co-polymer gelling additive in the composition may affect the thermal properties of the PCM and the rheological properties of the composition. The thermal properties of the PCM which are influenced by the amounts of gelling additives may include the subcooling and the latent heat. Without being bound by theory, an excess of styrene co-polymer gelling additive (i.e. a weight ratio to silica gelling additive of less than 0.6:1) may interfere with the crystal structure of the PCM and lead to a diminished latent heat and pronounced subcooling. The presence of the silica gelling additive can prevent such thermal drawbacks and yield desired thermal properties.

It is desired in some PCM applications that the composition shows a solid-like behavior at rest i.e. when no external shear stress is applied. Without the presence of silica gelling additive, it is difficult to achieve this rheological behavior since the presence of styrene co-polymer gelling additive alone may allow the composition to flow at rest slowly due to its own weight even at moderate temperatures. Such behavior is undesired in many applications where the PCM is packed in a container. Such flow at rest can be stopped by the combination of gelling additives according to the invention. Moreover, by using the weight ratio of gelling agents of the invention, the same solid-like behavior can be obtained even at relatively high temperatures.

Article Comprising the Composition

In one aspect, the invention provides an article comprising a sealed container and a composition according to the invention contained within the container. The gel properties of the composition may allow the container to have a thinner and/or less permeable wall than otherwise required (i.e. the container may weigh less) or the container may be made with a different (e.g. cheaper) material or sealing method.

The container may be made of metal or plastic, preferably plastic. The container may be made of a plastic selected from polyamides, polyamines, polyimides, polyacrylics, polycarbonates, polydienes, polyepoxides, polyesters, polyethers, polyfluorocarbons, formaldehyde polymers, natural polymers, polyolefins, fluorinated polyolefins, polyphenylenes, silicon containing polymers, polyurethanes, polyvinyls, polyacetals, polyacrylates and copolymers and mixtures thereof. Preferably the plastic is selected from polyolefins, polyvinyls, polyesters and co-polymers and mixtures thereof. The container may be made of a metal selected from steel, aluminium, titanium, bronze, copper, silver, magnesium and alloys thereof, preferably the metal is selected from aluminium and alloys thereof.

The container may be rigid or flexible. The container may be a rod, a pouch or a panel, preferably a pouch or a panel. Preferably the container is a flexible pouch. The container may be a rigid panel.

Product Comprising the Composition

The composition of the invention may be incorporated in a textile product (e.g. an article of clothing), foam product (e.g. a mattress), packaging product (e.g. a container for heat-sensitive material), electronic product (e.g. a printed circuit board, microchip, CPU or battery), automotive system (e.g. a vehicle engine component), refrigeration system (e.g. a refrigerator or freezer), heating, ventilation and air-conditioning (HVAC) system or construction material.

In one aspect of the invention, there is provided a textile product, foam product, medical product, electronic product, packaging product, automotive system, refrigeration system, HVAC system or construction material comprising the composition of the invention.

Method

In one aspect; the invention provides a method of making the composition of the invention comprising the steps of:
  i) mixing the components of the composition at a sufficient temperature and for a sufficient time to allow the styrene co-polymer gelling additive to completely dissolve in the composition; and
  ii) stopping mixing to allow the composition to rest and to form a gel.

Step i) may produce a uniform composition, preferably a homogeneous composition.

Step ii) may produce a uniform composition, preferably a homogeneous composition.

Step i) may comprise heating. The temperature in step i) may be at least 20° C., preferably at least 30° C. more preferably at least 50° C., yet more preferably at least 70° C., particularly at least 90° C., The temperature in step i) may be at most 160° C., preferably at most 140° C., more preferably at most 120° C., particularly at most 110° C.

The duration of step i) may be at least 30 mins, preferably at least 40 mins, more preferably at least 60 mins, particularly at least 80 mins. The duration of step i) may be at most 24 hours, preferably at most 15 hours, more preferably at most 10 hours, particularly at most 6 hours.

The mixing may be by agitation. The agitation may be stirring at a speed of at least 100 rpm, preferably at least 200 rpm, more preferably at least 300 rpm, particularly at least 400 rpm. The agitation may be stirring at a speed of at most 1500 rpm, preferably at most 1300 rpm.

Step ii) may comprise stopping heating. The temperature in step ii) may be ambient temperature. The temperature in step i) may be at least 20° C. The temperature in step i) may be at most 80° C., preferably at most 60° C., more preferably at most 40° C., particularly at most 30° C.

The duration of step ii) may be at least 30 mins, preferably at least 40 mins, more preferably at least 60 mins, particularly at least 80 mins. The duration of step ii) may be at most 48 hours, preferably at most 24 hours, more preferably at most 15 hours, particularly at most 10 hours.

Use

In one aspect, the present invention provides the use of a combination of a silica gelling additive and a styrene co-polymer gelling additive to make a gel composition comprising a phase change material wherein the flow at rest (FAR) period at 25° C., as measured herein, of the gel composition is at least 2 times longer than that of a comparative gel composition wherein the comparative gel composition comprises a comparative gelling additive consisting solely of the styrene co-polymer, wherein the total wt % of gelling additives in the gel composition and in the comparative gel composition is equivalent.

The FAR period at 25° C. of the gel composition may be at least 4 times longer than that of the comparative gel composition, preferably at least 6 times longer, more preferably at least 8 times longer, particularly at least 10 times longer.

The FAR period at 40° C. of the gel composition may be at least 4 times longer than that of the comparative gel composition, preferably at least 6 times longer, more preferably at least 8 times longer, particularly at least 10 times longer.

In another aspect, the present invention provides the use of a combination of a silica gelling additive and a styrene co-polymer gelling additive to make a gel composition comprising a phase change material wherein the shear thinning value (STV) at 25° C., as measured herein, of the gel composition is at least 2 times greater than that of a comparative gel composition wherein the comparative gel composition comprises a comparative gelling additive consisting solely of the styrene co-polymer, wherein the total wt % of gelling additives in the gel composition and in the comparative gel composition is equivalent.

The STV at 25° C. of the gel composition may be at least 4 times greater than that of the comparative gel composition, preferably at least 6 times greater, more preferably at least 8 times greater, particularly at least 10 times greater.

The STV at 40° C. of the gel composition may be at least 4 times greater than that of the comparative gel composition, preferably at least 6 times greater, more preferably at least 8 times greater, particularly at least 10 times greater.

EXAMPLES

The invention is illustrated by the following non-limiting examples.

It will be understood that all tests and physical parameters described herein have been determined at atmospheric pressure and room temperature (i.e. about 25° C.), unless otherwise stated herein, or unless otherwise stated in the referenced test methods and procedures. All parts and percentages are given by weight unless otherwise stated. All rheology measurements have been performed after the samples were allowed to rest for at least 1 day after sample making.

Test Methods

In this specification, the following test methods have been used:

(i) Flow At Rest (FAR) was measured by placing an amount of the sample in a plastic conical funnel with a circular lower (outlet) aperture of 0.9 cm diameter, a circular upper (inlet) aperture of 6.8 cm diameter and a height of 5 cm. The FAR was measured as the time elapsed for 85 wt % of the sample to flow through the outlet aperture. The experiment was performed at 25° C. and at 40° C.

(ii) Differential Scanning calorimetry (DSC) was performed using a Mettler-Toledo machine (module DSC822-LT and 3+) and the control and analysis software provided by Mettler-Toledo. DSC may be used to measure for example, melting points, crystallisation points and latent heats.

(iii) Rheological properties of the samples were measured with a DHR-2 Rheometer from TA Instruments. The shear rate sweep measurements were performed at 25° C. and at 40° C. with a 40 mm stainless steel parallel plate geometry. Neat PCM—Control A sample of neat CrodaTherm 6.5 (ex Croda Europe Limited), a fatty acid ester PCM, was used as the control sample. With a melting point of 6.84° C., it is in liquid form at room temperature (i.e. about 25° C.).

Example 1—Comparative

A comparative sample gel comprising 91.7 wt % CrodaTherm 6.5 and 8.3 wt % Kraton A1535 (ex Kraton Corporation) was made by the following steps:
1) The CrodaTherm 6.5 is heated to 100° C. in a beaker while stirring with an overhead stirrer at 500 rpm.
2) Stirring speed is set to 750 rpm and Kraton A1535 is added over 40 mins.
3) When all Kraton is added, the mixture is stirred for another 40 mins to fully homogenize the composition.
4) The agitation is stopped and the composition is allowed to rest and cool down and form a gel.

Example 2

A sample gel comprising:
a) 91.7 wt % CrodaTherm 6.5;
b) 5.3 wt % hydrophilic fumed silica; and
c) 3 wt % Kraton A1535
was made by following the procedure explained in Example 1 and adding the following steps between step 1) and step 2):
1a) Hydrophilic fumed silica is added gradually while stirring speed is raised to 1200 rpm.
1b) When all silica is added the mixture is stirred for another 5 mins.

Example 3

A sample gel comprising:
a) 91.2 wt % CrodaTherm 6.5 and 0.5 wt % nucleating agent;
b) 5 wt % hydrophilic fumed silica;
c) 3 wt % Kraton A1535; and
d) 0.3 wt % PEG400, a polyethylene glycol.
was made by following the procedure explained in Example 2 and adding the following step after step 3:
3a) Stirring speed is set to 600 rpm and PEG400 is added drop by drop.

Example 4

The above samples were tested using the test methods defined herein. Results obtained from the tests of the samples are given in Table 1 below,

TABLE 1

|  |  | Neat PCM - Control | Example 1 - Comparative | Example 2 | Example 3 |
|---|---|---|---|---|---|
| Crystallization point (° C.) |  | 2.60 | 1.42 | 1.82 | 3.48 |
| Melting point (° C.) |  | 6.84 | 4.87/6.98[a] | 6.13 | 6.34 |
| Latent heat (J/g) |  | 178.7 | 153.6 | 156 | 156.9 |
| Viscosity at 25° C. (Pa · s) | at 0.2 s$^{-1}$ | N/A[b] | 668 | 222 | 798 |
|  | at 59 s$^{-1}$ | 0.013 | 107 | 0.89 | 4.79 |
| Shear Thinning Value (STV) at 25° C. (viscosity at 0.2 s$^{-1}$/ viscosity at 59 s$^{-1}$) |  | N/A | 6.24 | 249 | 167 |
| Viscosity at 40° C. (Pa · s) | at 0.2 s$^{-1}$ | N/A[b] | 4.6 | 243 | 839 |
|  | at 59 s$^{-1}$ | 0.011 | 4.0 | 0.78 | 3.76 |
| STV at 40° C. |  | N/A | 1.15 | 312 | 223 |
| Flow At Rest (FAR) | at 25° C. | N/A | 26 mins | >1 day | >1 day |
|  | at 40° C. | N/A | 7 mins | >1 day | >1 day |

[a]two melting peaks were observed
[b]measurement was lower than the equipment minimum limit - Newtonian behaviour is expected.

In Examples 1 to 3, the total wt % of gelling additives in the compositions is kept constant and equivalent in order to make an adequate comparison.

The combination of gelling additives in Examples 2 & 3 according to the invention demonstrates clear advantages over comparative Example 1 in thermal properties such as a diminished decrease in crystallization temperature and a uniform melting peak.

The gellants used in all Examples increase the viscosity when compared with the neat PCM. In addition the inventive compositions in Examples 2 & 3 demonstrate pronounced shear thinning even at 25° C. This can be seen by comparing the Shear Thinning Value (STV) results for Examples 2 & 3 with Example 1. High shear thinning at low temperatures is particularly interesting for many manufacturers to process the material.

In many PCM applications, it is desirable to prevent the PCM composition from flowing when the packaging material is accidentally punctured during usage or transportation. The Flow At Rest (FAR) test results show the advantages of Examples 2 & 3 in this respect when compared with Example 1. Even at 40° C., the compositions of Example 2 and Example 3 do not flow through the orifice, unlike Example 1.

It is to be understood that the invention is not to be limited to the details of the above embodiments, which are described by way of example only. Many variations are possible.

The invention claimed is:

1. A composition comprising:
a) a phase change material;
b) 1 to 10 wt % of a silica gelling additive;
c) a styrene co-polymer gelling additive;
wherein the composition is in a gel form and wherein a weight ratio of b) silica gelling additive to c) styrene co-polymer gelling additive in the composition is in a range of from 0.6 to 5:1; and
d) 0.05 to 10 wt % of a diol, wherein the diol is a polyethylene glycol.

2. A composition according to of claim 1 wherein the phase change material is a fatty acid, a fatty alcohol, a fatty amine, a fatty acid ester, a fatty alcohol ester, a fatty acid amide, or mixture thereof.

3. The composition of claim 1 wherein the phase change material comprises an ester.

4. The composition of claim 1, wherein the composition comprises at least 60 wt % of phase change material.

5. The composition of claim 1, wherein the silica gelling additive is a fumed silica.

6. The composition of claim 1, wherein the styrene co-polymer gelling additive is a styrene-(ethylene-propylene)-styrene (SEPS) tri-block co-polymer, a styrene-(ethylene-butylene)-styrene (SEBS) tri-block co-polymer, or a mixture thereof.

7. The composition of claim 1, further comprising a nucleating agent, wherein the nucleating agent has a melting point at least 15° C. higher than that of the phase change material.

8. The composition of claim 1, where the composition exhibits a flow at rest (FAR) period at 25° C. of at least 30 minutes, wherein the flow at rest period is defined as a time needed for 85 wt % of a sample of the composition to flow out of a conical funnel through a lower circular aperture, when the sample is placed into the conical funnel, the conical funnel being defined by a circular lower outlet aperture having a 0.9 cm diameter, a circular upper inlet aperture of 6.8 cm diameter, and a height of 5 cm.

9. The composition of claim 1, wherein the composition is a shear thinning gel composition.

10. The composition of claim 9, wherein the composition exhibits a shear thinning value (STV) at 25° C. of at least 20, wherein the shear thinning value (STV) is defined as:

$$STV = \text{viscosity at } 0.2s^{-1}/\text{viscosity at } 59s^{-1}$$

and the viscosities at $0.2\ s^{-1}$ and at $59\ s^{-1}$ are measured at 25° C. on a rheometer with a 40 mm stainless steel parallel plate geometry.

11. An article comprising a sealed container containing the composition of claim 1.

12. The article of claim 11 wherein the sealed container is a pouch or panel.

13. A product comprising the composition of claim 1, wherein the product is a textile product, a foam product, a medical product, an electronic product, a packaging product, an automotive system, a refrigeration system, an HVAC system, or a construction material.

14. A method of making a composition of claim 1, the method comprising:
  i) mixing the phase change material, the silica gelling additive, and the styrene co-polymer gelling additive at a sufficient temperature and for a sufficient time to allow the styrene co-polymer gelling additive to completely dissolve in the composition; and
  ii) stopping mixing to allow the composition to rest and to form a gel.

* * * * *